(12) United States Patent
Zhang et al.

(10) Patent No.: US 7,135,593 B2
(45) Date of Patent: Nov. 14, 2006

(54) DEGRADABLE CROSSLINKERS, AND DEGRADABLE CROSSLINKED HYDROGELS COMPRISING THEM

(75) Inventors: Hongmin Zhang, Duxbury, MA (US); Alexander Schwarz, Brookline, MA (US)

(73) Assignee: Biosphere Medical, Inc., Rockland, MA (US)

( * ) Notice: Subject to any disclaimer, the term of this patent is extended or adjusted under 35 U.S.C. 154(b) by 248 days.

(21) Appl. No.: 10/806,036

(22) Filed: Mar. 22, 2004

(65) Prior Publication Data
US 2005/0113285 A1   May 26, 2005

Related U.S. Application Data

(62) Division of application No. 10/186,251, filed on Jun. 27, 2002, now Pat. No. 6,713,646.

(60) Provisional application No. 60/372,264, filed on Apr. 12, 2002.

(51) Int. Cl.
C07C 96/52 (2006.01)
C07C 239/00 (2006.01)
C08F 20/00 (2006.01)

(52) U.S. Cl. .............. 560/205; 560/312; 526/328
(58) Field of Classification Search ............ 516/99; 560/205, 312; 526/328
See application file for complete search history.

(56) References Cited

U.S. PATENT DOCUMENTS

| | | | |
|---|---|---|---|
| 3,718,716 A | 2/1973 | Joh et al. | 260/898 |
| 3,858,510 A | 1/1975 | Kai et al | 101/395 |
| 4,160,077 A * | 7/1979 | Brooks et al. | 525/32 |
| 5,124,421 A * | 6/1992 | Ulbrich et al. | 526/212 |
| 5,130,479 A | 7/1992 | Ulbrich et al. | 562/874 |
| 5,545,681 A * | 8/1996 | Honkonen | 524/115 |
| 5,922,612 A | 7/1999 | Alder et al. | 436/163 |
| 6,323,360 B1 | 11/2001 | Ruckenstein et al. | 560/199 |

FOREIGN PATENT DOCUMENTS

| WO | WO 01/44307 A2 | 6/2001 |
|---|---|---|
| WO | WO 01/68720 A1 | 9/2001 |
| WO | WO 01/68722 A1 | 9/2001 |

OTHER PUBLICATIONS

Argade et al.; "Preparation and Characterization of Novel Biodegradable tri-and tetraacrylate Intermediates", Polymer Bulletin 31:401-407, (1993).
Bruining et al.; "Biodegradable Three-Dimensional Networks of Poly(dimethylamino ethyl methacrylate). Synthesis, Characterization and in Vitro Studies of Structural Degradation and Cytotoxicity", Biomaterials 21: 595-604, (2000).
Bruining et al.; "New Biodegradable Networks of Poly(N-vinylpyrrolidinone) Designed for controlled Nonburst Degradation in the Vitrreous Body", J Biomed. Mater. Res. 47:189-197, (1999).

(Continued)

*Primary Examiner*—David W. Wu
*Assistant Examiner*—Michael Bernshteyn
(74) *Attorney, Agent, or Firm*—Dana M. Gordon; Foley Hoag LLP

(57) ABSTRACT

One aspect of the present invention relates to base-labile crosslinkers. A second aspect of the present invention relates to degradable crosslinked polymers and hydrogels comprising a base-labile crosslinker. The present invention also relates to a method of influencing the degradation rate of a crosslinked polymer or hydrogel, comprising the step of incorporating uncharged acrylamides into the crosslinked polymer or hydrogel.

43 Claims, 5 Drawing Sheets

Five New Crosslinkers

New Crosslinkers (NCL)

n=1, N,N'-(Dimethacryloyloxy)malonamide (C3NCL)

n=2, N,N'-(Dimethacryloyloxy)succinamide (C4NCL)

n=3, N,N'-(Dimethacryloyloxy)glutarylamide (C5NCL)

n=4, N,N'-(Dimethacryloyloxy)adipamide (C6NCL)

n=6, N,N'-(Dimethacryloyloxy)suberoylamide (C8NCL)

OTHER PUBLICATIONS

Eo, Akala; "Hydrolysis of Linear Copolymers with Pendant N, O-diacylhydroxylamine Moieties)", Pharm. Pharmacol. Lett. 8(3): 129-132, (1998).

Grosse-Sommer and Prud'homme; "Degradable Phosphazene-crosslinked Hydrogels", Journal of Controlled Release 40: 261-267, (1996).

Gombotz and Petit; "Biodegradable Polymers for Protein and Peptide Drug Delivery". Bioconjugate Chem. 6: 332-351, (1995).

Ulbrich et al.; "Novel Biodegrdable Hydrogels Prepared Using the divinyl;ic Crosslinking Agent N, O-dimethacryloydroxylamine. 1. Synthesis and Characterization of Rates of Gel Degradation, and Rate of Release of Model Drugs, in Vitro and Vivo", Journal of controlled Release 24: 181-19, (1993).

Ruckenstein and Zhang; "A Novel Breakable Cross-Linker and pH-Responsive Star-Shaped and Gel Polymers", Macromelecules 32: 3979-3983, (1999).

Sawhney et al.; "Biocrodible Hydrogels Based on Photopolymerized Poly(ethylene glycol)-co-poly($\alpha$hydroxy acid) diacrylate Macromers", Macromolecules 26: 581-587, (1993).

Ulbrich et al.; "Synthesis Of Novel Hydrolytically degradable Hydrogels for Controlled Drug Release", Journal of Controlled Release 34: 155-165, (1995).

* cited by examiner

Five New Crosslinkers

New Crosslinkers (NCL)

n=1, N,N'-(Dimethacryloyloxy)malonamide (C3NCL)

n=2, N,N'-(Dimethacryloyloxy)succinamide (C4NCL)

n=3, N,N'-(Dimethacryloyloxy)glutarylamide (C5NCL)

n=4, N,N'-(Dimethacryloyloxy)adipamide (C6NCL)

n=6, N,N'-(Dimethacryloyloxy)suberoylamide (C8NCL)

Synthesis of Star-shaped New Crosslinker

Three-arm Star-shaped NCL

EXAMPLES OF POSSIBLE NEW DEGRADABLE CROSSLINKERS

Linear alphatic type:

Linear aromatic type:

Star aromatic type:

Star alphatic type:

Synthesis of an Acrylamide Type Crosslinker

DEGRADABLE CROSSLINKERS, AND DEGRADABLE CROSSLINKED HYDROGELS COMPRISING THEM

RELATED APPLICATIONS

This application is a divisional of U.S. patent application Ser. No. 10/186,251, filed Jun. 27, 2002, now U.S. Pat. No. 6,713,646; which claims the benefit of the filing date of U.S. Provisional Patent Application Ser. No. 60/372,264, filed Apr. 12, 2002.

BACKGROUND OF THE INVENTION

Biocompatible polymeric materials have been used extensively in medical implant devices. For some applications, the polymers should not only be biocompatible but also degradable, into non-toxic products (bone fixtures, sutures, drug containing implants etc.). This degradability removes the need to later remove the device from the implant site.

The first degradable polymers were based on hydrophobic polymers like PLGA, poly(orthoesters), polyanhydrides and polyiminocarbonates, which degrade hydrolytically into water-soluble monomers and oligomers. The degradation times can be adjusted by the chemical composition of these polymers. The problem with these polymers is the need to keep them completely dry during storage. The majority of degradable polymers are essentially hard, brittle materials, developed for drug delivery uses.

Other degradable polymers are based on naturally-occurring polymers, e.g., polysaccharides or polypeptides. The degradation process is based on enzymatic hydrolysis of the polysaccharides or polypeptides. While these products can be formed as hydrogels, and therefore may be stored in an aqueous environment, the degradation time is not controllable due to variable enzyme expression in humans. Additionally, only the unmodified part of the protein or polysaccharide is degradable, while modified sites are nondegradable. Furthermore, naturally derived products have to undergo vigorous testing to ensure that they are free of endotoxins and contaminating proteins. For human or animal derived proteins, viral contamination is a constant worry.

Another approach is to synthesize a hydrogel, which contains an unstable crosslinker. This approach has been investigated by a number of groups. The first approach was to polymerize the hydrogel in situ using photopolymerization of monomers that contain a hydrolytically unstable lactic acid component. The degradation time can be adjusted through the numbers of lactic acid units incorporated into the monomer. However, these monomers must be stored under anhydrous conditions.

Another approach has been to synthesize crosslinkers containing hydrolytically labile carbonate (Bruining et al, Biomaterials 21 (2000) 595–604), ester (Argade et al, Polymer Bulletin 31 (1993) 401–407), and phosphazene linkers (Grosse-Sommer et al, Journal of Controlled Release 40 (1996) 261–267). These hydrogels are not stable under any of the conditions described and start to degrade immediately following synthesis and placement into an aqueous environment. Yet another approach utilizes a reduction/oxidation cleavable crosslinker, such as a disulfide bridge. However, the reduction product from the disulfide bridge is two thiols, which are easily reoxidized to the disulfide bridge, restoring the crosslink.

Still another approach would use a crosslinker that is stable under either basic or acidic conditions, and starts to degrade at blood pH of pH 7.4. Ruckenstein et al (Ruckenstein et al, Macromolecules, 32 (1999) 3979–3983; U.S. Pat. No. 6,323,360) described one such crosslinker as the addition product between ethylene glycol divinyl ether and methacrylic acid. The resulting crosslinker, containing hemiacetal functional groups, is base stable and degrades under acidic conditions. However, the publication does not provide a means to control the degradation time nor are the described degradation conditions in organic solvents useful for biological applications.

Another degradable crosslinker has been described by Ulbrich (Ulbrich et al, Journal of Controlled Release, 24 (1993) 181–190; Ulbrich et al, Journal of Controlled Release, 34 (1995) 155–165; U.S. Pat. No. 5,130,479; 5,124,421). The crosslinker is N,O-dimethacryloylhydroxylamine. The degradation of this crosslinker is based on the base-catalyzed Lossen rearrangement of substituted hydroxamic acids. The crosslinker appears to be stable under acidic conditions, while degradation occurs at neutral to basic pH values. The only way described in the articles and patents by Ulbrich et al to control degradation is through the crosslink density. Increasing the crosslink density from 1.2% to 2.4% increases the degradation time from 21 hours to 45 hours at pH 7.4 (U.S. Pat. No. 5,124,421). Akala (Akala, Pharm Pharmacol Lett 8 (1998) 129–132) discovered that the introduction of acrylic acid groups into a linear polymer accelerated the degradation of the pendant N,O-diacylhydroxyamine moieties, an effect not reported by Ulbrich et al.

SUMMARY OF THE INVENTION

One aspect of the present invention relates to base-labile crosslinkers. A second aspect of the present invention relates to degradable crosslinked polymers and hydrogels comprising a base-labile crosslinker. The present invention also relates to a method of influencing the degradation rate of a crosslinked polymer or hydrogel, comprising the step of incorporating uncharged acrylamides into the crosslinked polymer or hydrogel.

DETAILED DESCRIPTION OF THE INVENTION

Figure 1:
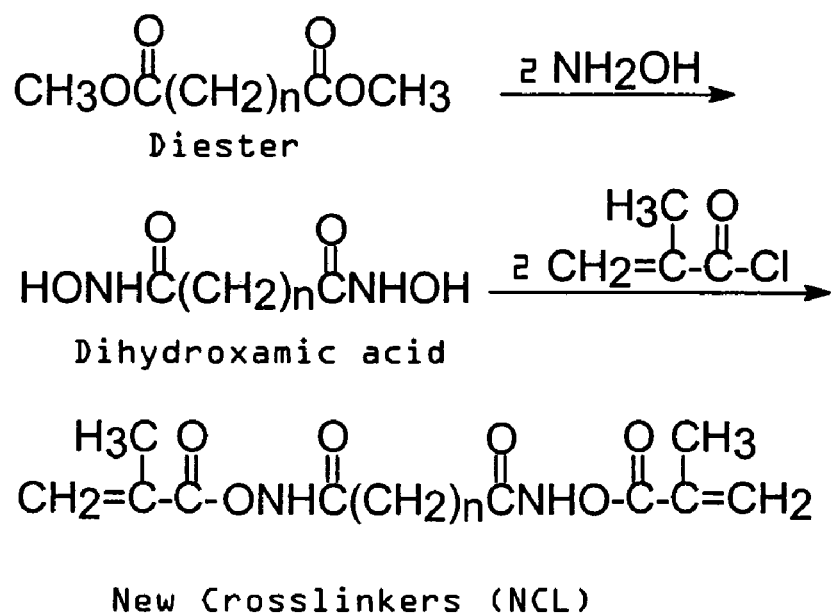
FIG. 1 depicts a general synthetic scheme for certain compounds of the present invention.
Figure 2:
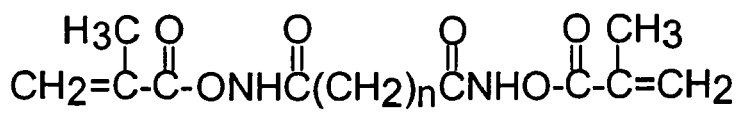
FIG. 2 depicts five compounds of the present invention.
Figure 3:
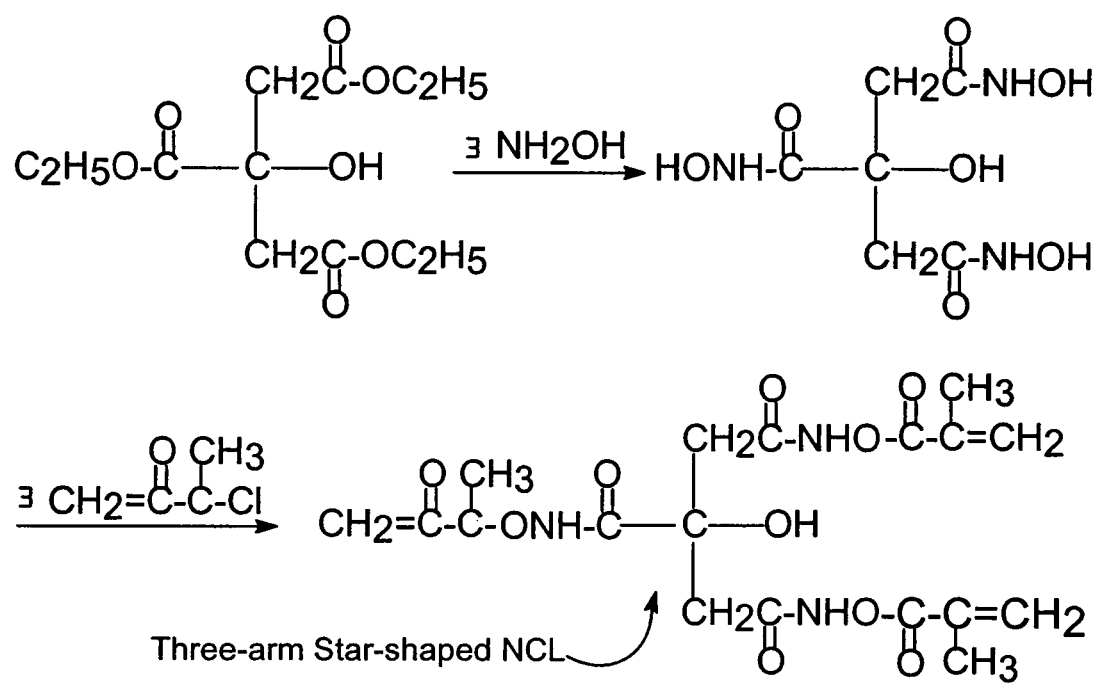
FIG. 3 depicts a synthetic scheme for a compound of the present invention
Figure 4:
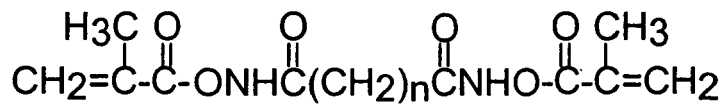
FIG. 4 depicts various structural classes of compounds of the present invention.
Figure 4:
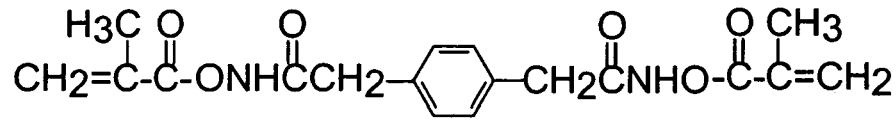
Figure 4:
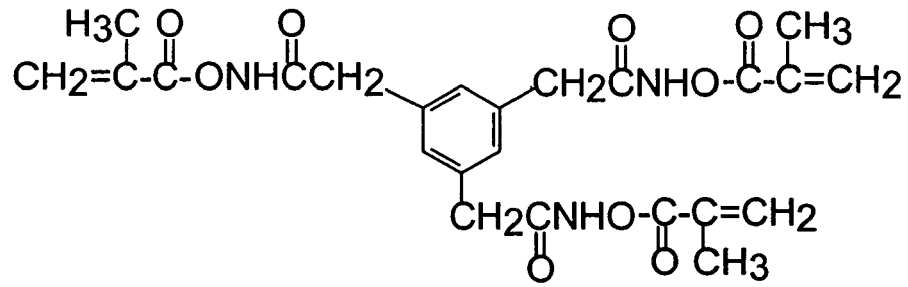
Figure 4:
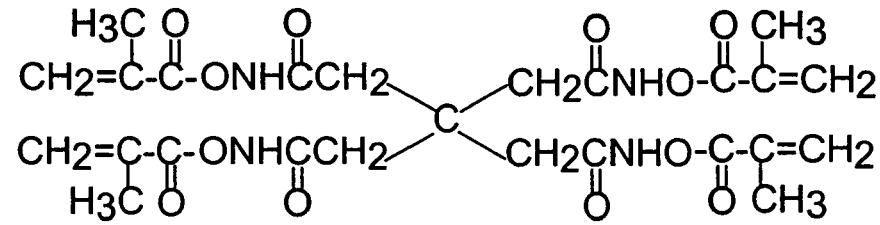
Figure 5:
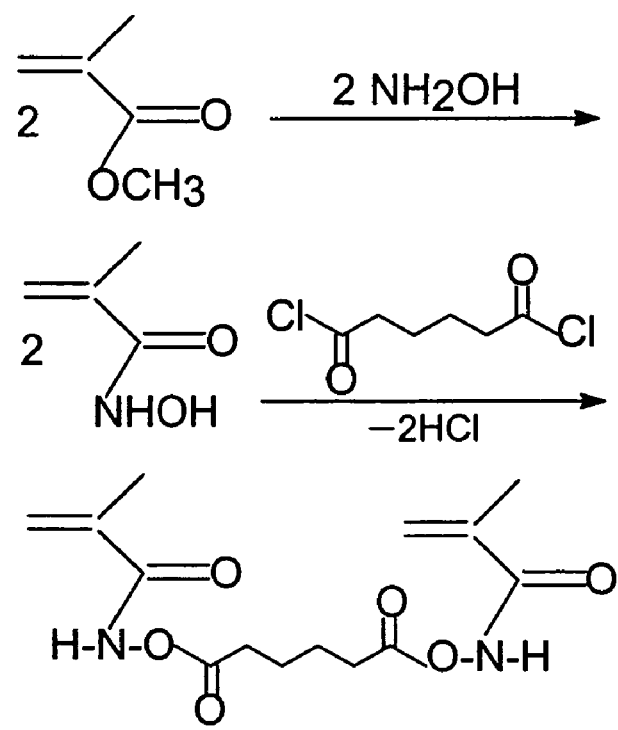
FIG. 5 depicts a synthetic scheme for an acrylamide type crosslinker.

Remarkably, we have discovered that the presence of certain acrylamides in a crosslinked polymer comprising acid- or base-labile crosslinkers can influence the degradation rate of the polymers, while the presence of other acrylamides, e.g., Trisacrylamide, Trisacrylate, and hydroxyethyl acrylate, does not have a significant effect on the polymer degradation rate. This result stands in contrast to Akalo (Akalo, Pharm Pharmacol Lett 8 (1998) 129–132), who showed that the degradation rate can be controlled by incorporation of acrylic acid.

One aspect of the present invention relates to base-labile crosslinkers. A second aspect of the present invention relates to degradable crosslinked polymers and hydrogels comprising a base-labile crosslinker. The present invention also relates to a method of influencing the degradation rate of a crosslinked polymer or hydrogel, comprising the step of incorporating uncharged acrylamides into the crosslinked polymer or hydrogel.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "crosslinking agent", as used herein, refers to any chemical agent that joins adjacent chains of a polymer through covalent bonds.

The term "initiator", as used herein, refers to any compound which initiates polymerization, or produces a reactive species which initiates polymerization.

The term "polymer", as used herein, refers to a natural or synthetic compound of unusually high molecular weight consisting of a repeating monomeric unit.

The term "polymerization", as used herein, refers to the bonding of two or more monomers to form a polymer.

The term "monomer", as used herein, refers to a molecule that can combine with another to form a polymer; it is the repeating unit of a polymer.

The term "biocompatible", as used herein, refers to having the property of being biologically compatible by not producing a toxic, injurious, or immunological response in living tissue.

The term "degradable", as used herein, refers to having the property of breaking down or degrading under certain conditions, e.g., at neutral or basic pH.

The term "gel", as used herein, refers to a colloid in which the disperse phase has combined with the dispersion medium to produce a semisolid material.

The term "colloid", as used herein, refers to a suspension of finely divided particles in a continuous medium in which the particles are approximately 5 to 5,000 angstroms in size.

The term "hydrogel", as used herein refers to a type of gel in which the disperse phase has combined with water to produce a semisolid material.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

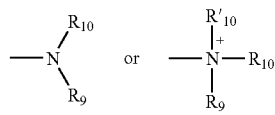

wherein $R_9$, $R_{10}$ and $R'_{10}$ each independently represent a group permitted by the rules of valence.

The term "acylamino" is art-recognized and refers to a moiety that can be represented by the general formula:

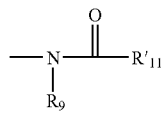

wherein $R_9$ is as defined above, and $R'_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

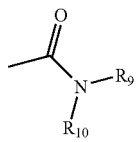

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

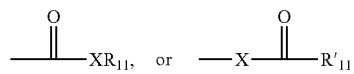

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, the present invention relates to a compound represented by 1:

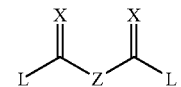

wherein

X represents independently for each occurrence O or S;

L represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1–10; and m represents independently for each occurrence an integer in the range 0–10.

In certain embodiments, the present invention relates to a compound represented by 1 and the attendant definitions, wherein X represents O.

In certain embodiments, the present invention relates to a compound represented by 1 and the attendant definitions, wherein L represents —NH—O—Q.

In certain embodiments, the present invention relates to a compound represented by 1 and the attendant definitions, wherein L represents —O—NH—Q.

In certain embodiments, the present invention relates to a compound represented by 1 and the attendant definitions, wherein Q represents acryloyl, or 2-methacryloyl.

In certain embodiments, the present invention relates to a compound represented by 1 and the attendant definitions, wherein R represents H.

In certain embodiments, the present invention relates to a compound represented by 1 and the attendant definitions, wherein Z represents (CR$_2$)$_n$.

In certain embodiments, the present invention relates to a compound represented by 1 and the attendant definitions, wherein X represents O; and L represents —NH—O—Q.

In certain embodiments, the present invention relates to a compound represented by 1 and the attendant definitions, wherein X represents O; and L represents —O—NH—Q.

In certain embodiments, the present invention relates to a compound represented by 1 and the attendant definitions, wherein X represents O; L represents —NH—O—Q; and Q represents acryloyl, or 2-methacryloyl.

In certain embodiments, the present invention relates to a compound represented by 1 and the attendant definitions, wherein X represents O; L represents —O—NH—Q; and Q represents acryloyl, or 2-methacryloyl.

In certain embodiments, the present invention relates to a compound represented by 1 and the attendant definitions, wherein X represents O; L represents —NH—O—Q; Q represents acryloyl, or 2-methacryloyl; and R represents H.

In certain embodiments, the present invention relates to a compound represented by 1 and the attendant definitions, wherein X represents O; L represents —O—NH—Q; Q represents acryloyl, or 2-methacryloyl; and R represents H.

In certain embodiments, the present invention relates to a compound represented by 1 and the attendant definitions, wherein X represents O; L represents —NH—O—Q; Q represents acryloyl, or 2-methacryloyl; R represents H; and Z represents $(CR_2)_n$.

In certain embodiments, the present invention relates to a compound represented by 1 and the attendant definitions, wherein X represents O; L represents —O—NH—Q; Q represents acryloyl, or 2-methacryloyl; R represents H; and Z represents $(CR_2)_n$.

In certain embodiments, the present invention relates to a method of preparing a compound represented by 1 and the attendant definitions comprising reacting at least 2 molar equivalents of a hydroxylamine with a diester thereby forming a dihydroxamic acid; and reacting the dihydroxamic acid with at least 2 molar equivalents of an acryloyl halide.

In certain embodiments, the present invention relates to a compound represented by 2:

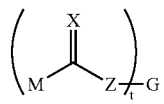

wherein

X represents independently for each occurrence O or S;

M represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)_n$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;

R represents independently for each occurrence H or alkyl;

Z represents $(CR_2)_n$, $(CR_2)_n$J$(CR_2)_m$, or $(CR_2)_n$Ar$(CR_2)_m$;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1–10; and t represents 3 or 4.

In certain embodiments, the present invention relates to a compound represented by 2 and the attendant definitions, wherein X represents O.

In certain embodiments, the present invention relates to a compound represented by 2 and the attendant definitions, wherein M represents —NH—O—Q.

In certain embodiments, the present invention relates to a compound represented by 2 and the attendant definitions, wherein M represents —O—NH—Q.

In certain embodiments, the present invention relates to a compound represented by 2 and the attendant definitions, wherein Q represents acryloyl, or 2-methacryloyl.

In certain embodiments, the present invention relates to a compound represented by 2 and the attendant definitions, wherein R represents H.

In certain embodiments, the present invention relates to a compound represented by 2 and the attendant definitions, wherein X represents O; and M represents —NH—O—Q.

In certain embodiments, the present invention relates to a compound represented by 2 and the attendant definitions, wherein X represents O; and M represents —O—NH—Q.

In certain embodiments, the present invention relates to a compound represented by 2 and the attendant definitions, wherein X represents O; M represents —NH—O—Q; and Q represents acryloyl, or 2-methacryloyl.

In certain embodiments, the present invention relates to a compound represented by 2 and the attendant definitions, wherein X represents O; M represents —O—NH—Q; and Q represents acryloyl, or 2-methacryloyl.

In certain embodiments, the present invention relates to a compound represented by 2 and the attendant definitions, wherein X represents O; M represents —NH—O—Q; Q represents acryloyl, or 2-methacryloyl; and R represents H.

In certain embodiments, the present invention relates to a compound represented by 2 and the attendant definitions, wherein X represents O; M represents —O—NH—Q; Q represents acryloyl, or 2-methacryloyl; and R represents H.

In certain embodiments, the present invention relates to a method of preparing a compound represented by 2 and the attendant definitions comprising reacting at least 3 molar equivalents of a hydroxylamine with a triester or a tetraester thereby forming a trihydroxamic or tetrahydroxamic acid, respectively; and reacting the trihydroxamic or tetrahydroxamic acid with at least 3 molar equivalents of an acryloyl halide.

Polymers of the Invention

In certain embodiments, the present invention relates to a polymer, comprising a monomer represented by 1:

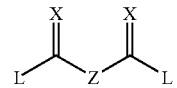

wherein

X represents independently for each occurrence O or S;

L represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)_n$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;

R represents independently for each occurrence H or alkyl;

Z represents $(CR_2)_n$, $(CR_2)_n$J$(CR_2)_m$, or $(CR_2)_n$Ar$(CR_2)_m$;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

n represents independently for each occurrence an integer in the range 1–10; and m represents independently for each occurrence an integer in the range 0–10.

In certain embodiments, the present invention relates to a polymer, comprising a monomer represented by 1 and the attendant definitions, wherein X represents O.

In certain embodiments, the present invention relates to a polymer, comprising a monomer represented by 1 and the attendant definitions, wherein L represents —NH—O—Q.

In certain embodiments, the present invention relates to a polymer, comprising a monomer represented by 1 and the attendant definitions, wherein L represents —O—NH—Q.

In certain embodiments, the present invention relates to a polymer, comprising a monomer represented by 1 and the attendant definitions, wherein Q represents acryloyl, or 2-methacryloyl.

In certain embodiments, the present invention relates to a polymer, comprising a monomer represented by 1 and the attendant definitions, wherein R represents H.

In certain embodiments, the present invention relates to a polymer, comprising a monomer represented by 1 and the attendant definitions, wherein Z represents $(CR_2)_n$.

In certain embodiments, the present invention relates to a polymer, comprising a monomer represented by 1 and the attendant definitions, wherein X represents O; and L represents —NH—O—Q.

In certain embodiments, the present invention relates to a polymer, comprising a monomer represented by 1 and the attendant definitions, wherein X represents O; and L represents —O—NH—Q.

In certain embodiments, the present invention relates to a polymer, comprising a monomer represented by 1 and the attendant definitions, wherein X represents O; L represents —NH—O—Q; and Q represents acryloyl, or 2-methacryloyl.

In certain embodiments, the present invention relates to a polymer, comprising a monomer represented by 1 and the attendant definitions, wherein X represents O; L represents —O—NH—Q; and Q represents acryloyl, or 2-methacryloyl.

In certain embodiments, the present invention relates to a polymer, comprising a monomer represented by 1 and the attendant definitions, wherein X represents O; L represents —NH—O—Q; Q represents acryloyl, or 2-methacryloyl; and R represents H.

In certain embodiments, the present invention relates to a polymer, comprising a monomer represented by 1 and the attendant definitions, wherein X represents O; L represents —O—NH—Q; Q represents acryloyl, or 2-methacryloyl; and R represents H.

In certain embodiments, the present invention relates to a polymer, comprising a monomer represented by 1 and the attendant definitions, wherein X represents O; L represents —NH—O—Q; Q represents acryloyl, or 2-methacryloyl; R represents H; and Z represents $(CR_2)_n$.

In certain embodiments, the present invention relates to a polymer, comprising a monomer represented by 1 and the attendant definitions, wherein X represents O; L represents —O—NH—Q; Q represents acryloyl, or 2-methacryloyl; R represents H; and Z represents $(CR_2)_n$.

In certain embodiments, the present invention relates to a polymer, comprising a monomer represented by 1 and the attendant definitions, further comprising a second monomer selected from the group consisting of acrylic acids, acrylates, and acrylamides.

In certain embodiments, the present invention relates to a polymer, comprising a monomer represented by 1 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

In certain embodiments, the present invention relates to a polymer, comprising a monomer represented by 2:

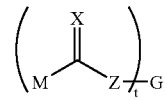

wherein

X represents independently for each occurrence O or S;

M represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_n$C(O)—, 2-alkylacryloylO$(CR_2)_n$C(O)—, 3-alkylacryloylO$(CR_2)_n$C(O)—, 2,3-dialkylacryloylO$(CR_2)_n$C(O)—, 3,3-dialkylacryloylO$(CR_2)_n$C(O)—, 2,3,3-trialkylacryloylO$(CR_2)_n$C(O)—, (diene)C(O)—, (vinyl)$(CR_2)_n$C(O)—, or (vinyl)ArC(O)—;

R represents independently for each occurrence H or alkyl;

Z represents $(CR_2)_n$, $(CR_2)_nJ(CR_2)_m$, or $(CR_2)_nAr(CR_2)_m$;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1–10; and t represents 3 or 4.

In certain embodiments, the present invention relates to a polymer, comprising a monomer represented by 2 and the attendant definitions, wherein X represents O.

In certain embodiments, the present invention relates to a polymer, comprising a monomer represented by 2 and the attendant definitions, wherein M represents —NH—O—Q.

In certain embodiments, the present invention relates to a polymer, comprising a monomer represented by 2 and the attendant definitions, wherein M represents —O—NH—Q.

In certain embodiments, the present invention relates to a polymer, comprising a monomer represented by 2 and the attendant definitions, wherein Q represents acryloyl, or 2-methacryloyl.

In certain embodiments, the present invention relates to a polymer, comprising a monomer represented by 2 and the attendant definitions, wherein R represents H.

In certain embodiments, the present invention relates to a polymer, comprising a monomer represented by 2 and the attendant definitions, wherein X represents O; and M represents —NH—O—Q.

In certain embodiments, the present invention relates to a polymer, comprising a monomer represented by 2 and the attendant definitions, wherein X represents O; and M represents —O—NH—Q.

In certain embodiments, the present invention relates to a polymer, comprising a monomer represented by 2 and the attendant definitions, wherein X represents O; M represents —NH—O—Q; and Q represents acryloyl, or 2-methacryloyl.

In certain embodiments, the present invention relates to a polymer, comprising a monomer represented by 2 and the attendant definitions, wherein X represents O; M represents —O—NH—Q; and Q represents acryloyl, or 2-methacryloyl.

In certain embodiments, the present invention relates to a polymer, comprising a monomer represented by 2 and the attendant definitions, wherein X represents O; M represents —NH—O—Q; Q represents acryloyl, or 2-methacryloyl; and R represents H.

In certain embodiments, the present invention relates to a polymer, comprising a monomer represented by 2 and the attendant definitions, wherein X represents O; M represents —O—NH—Q; Q represents acryloyl, or 2-methacryloyl; and R represents H.

In certain embodiments, the present invention relates to a polymer, comprising a monomer represented by 2 and the attendant definitions, further comprising a second monomer selected from the group consisting of acrylic acids, acrylates, and acrylamides.

In certain embodiments, the present invention relates to a polymer, comprising a monomer represented by 2 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

Gels and Hydrogels of the Invention

Hydrogels are a well recognized class of polymeric materials. These materials are characterized by their water-insolubility, hydrophilicity, high-water absorbability and swellable properties. The molecular components or units or segments of the hydrogel are characterized by a significant portion of hydrophilic components, units or segments, such as segments having ionic species or dissociable species such as acids (e.g., carboxylic acids, phosphonic acids, sulfonic acids, sulfinic acids, phosphinic acids, etc.), bases (e.g., amine groups, proton accepting groups), or other groups that develop ionic properties when immersed in water (e.g., sulfonamides). Acryloyl groups (and to a lesser degree methacryloyl groups) and the class of acrylic polymers, polymer chains containing or terminated with oxyalkylene units (such as polyoxyethylene chains or polyoxyethylene/polyoxypropylene copolymer chains) are also well recognized as hydrophilic segments that may be present within hydrophilic polymers.

Certain preferred water insoluble polymeric compositions useful in the present invention are listed below, although the entire class of hydrogel materials known in the art may be used to various degrees. The polymers set forth below and containing acid groups can be, as an option, partially or completely neutralized with alkali metal bases either as the monomer or the polymer or both. While the list below contains many of the preferred polymers which may be used in accordance with the present invention, the present invention is not limited to just these polymers and generally polymers traditionally understood as hydrogels by those skilled in the art can also be used: a) polyacrylic acid, polymethacrylic acid, polymaleic acid, copolymers thereof, and alkali metal and ammonium salts thereof; b) graft copolymers of starch and acrylic acid, starch and saponified acrylonitrile, starch and saponified ethyl acrylate, and acrylate-vinyl acetate copolymers saponified; c) polyvinyl alcohol, polyvinylpyrrolidone, polyvinyl alkylether, polyethylene oxide, polyacrylamide, and copolymers thereof; d) copolymers of maleic anhydride and alkyl vinylethers; and e) saponified starch graft copolymers of acrylonitrile, acrylate esters, vinyl acetate, and starch graft copolymers of acrylic acid, methylacrylic acid, and maleic acid.

The above exemplary polymers are cross-linked either during the polymerization or after the core is encapsulated. This cross-linking is achieved using the cross-linking agents of the present invention by methods known to those skilled in the art. This cross-linking can be initiated in the presence of radiation or a chemical free radical initiator.

One of the useful properties of hydrogels is their ability to absorb water and swell without dissolution of the matrix. As the hydrogel swells, the pore size of the hydrogel increases which enhances uptake of aqueous solutions and the diffusion of compounds out of the hydrogel. These properties have allowed use of hydrogels as controlled drug release systems and as absorbent materials. However, the rate of swelling of dried hydrogels upon exposure to an aqueous solution is limited by diffusion of water into the glassy polymer matrix. Conventional dried hydrogels have relatively small pore sizes resulting in slow swelling and release or absorption of liquids. The size of the pores in the hydrogel can be a factor used in the selection of hydrogels with the appropriate properties for the specific removable caps in the practice of the present invention. The larger the pore size, the generally higher rate of initial swelling a hydrogel undergoes.

Among the many hydrogel polymers which are useful as matrix polymers include poly(hydroxyalkyl methacrylate)s of which poly-(2-hydroxyethyl methacrylate), poly(glyceryl methacrylate) and poly(hydroxypropyl methacrylate) are well-known and identified in the literature as (P-HEMA), (P-GMA) and (P-(HPMA), respectively. Other hydrogel polymers include poly(acrylamide), poly(methacrylamide), poly(N-vinyl-2-pyrrolidine), and poly(vinyl alcohol), hydroxypropyl guar, high molecular weight polypropylene glycol or polyethylene glycol, and the like. It is known to produce sparingly cross-linked, water-insoluble but hydrophilic polymers which can be used as carriers for biologically active, at least slightly water-soluble substances by copolymerization of a major amount of hydrophilic mono-olefinic monomers and a minor amount ranging between 0.01 and 15% of said mono-olefinic monomers, of a low molecular weight cross-linker. As mono-olefinic monomers, particularly monoesters of acrylic or methacrylic acid with polyfunctional alcohols, such as ethyleneglycol monomethacrylate, and as cross-linking agents particularly diesters of said acids with said alcohols, such as ethyleneglycol bis-methacrylate are used and the copolymerization is carried out in the presence of water, see U.S. Pat. No. 3,220,960 or a water-free system, see U.S. Pat. No. 3,520,949. Low molecular as well as macromolecular, water-soluble substances, such as polyethyleneoxide mono-methacrylate together with a minor amount of the corresponding bis-methacrylate have been used (see U.S. Pat. No. 3,220,960) as monomers and cross-linking agents. The water-insoluble, but hydrophilic copolymers and the process for their production have been modified in several directions and adapted to specific purposes, e.g. the production of soft contact lenses, U.S. Pat. No. 3,220,960 and Reissue No. 27,401, and the copolymerization in the presence of linear polyamide resin in order to improve or modify the mechanical properties of shaped bodies formed from the obtained polymers, U.S. Pat. No. 3,520,949.

Non-limiting examples of the unsaturated monomers used as a starting material include those polymerizable monomers known to be soluble in water. Examples of these unsaturated monomer are: monomers containing an acid group, such as acrylic acid, beta-acryloyloxypropionic acid, methacrylic acid, crotonic acid, maleic acid, maleic anhydride, fumaric acid, itaconic acid, cinnamic acid, sorbic acid, 2-(meth)acryloylethane sulfonic acid, 2-(meth)acryloylpropane sulfonic acid, 2-(meth)acrylamido-2-methylpropane sulfonic acid, vinyl sulfonic acid, styrene sulfonic acid, allyl sulfonic acid, vinyl phosphonic acid and 2-(meth)acryloyloxyethyl phosphate, and alkaline metal salts and alkaline earth metal salts, ammonium salts, and alkyl amine salts thereof; dialkyl amino alkyl(meth)acrylates, such as N,N-dimethylaminoethyl(meth)acrylate and N,N-dimethylaminopropyl(meth)acrylate, and quaternary compounds thereof (for example, a reaction product produced with alkylhalide, and a reaction product produced with dialkyl sulfuric acid); dialkyl amino hydroxyalkyl(meth)acrylates, and quaternary compounds thereof; N-alkyl vinyl pyridine halide; hydroxyalkyl(meth)acrylates, such as hydroxymethyl (meth)acrylate, 2-hydroxyethyl(meth)acrylate, and 2-hydroxypropyl (meth)acrylate; acrylamide, methacrylamide, N-ethyl (meth)acrylamide, N-propyl(meth)acrylamide, N-isopropyl(meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloyl piperidine, and N-acryloyl pyrrolidine; vinyl acetate; and alkyl (meth)acrylates, such as methyl (meth)acrylate, and ethyl (meth)acrylate. These monomers may be used individually, or in combination.

Among the aforementioned monomers, unsaturated monomers containing an acrylate monomer as a chief constituent are preferred because the resulting water-absorbent resins have significantly improved water absorption characteristics. Here, the preferred acrylate monomers includes at least acrylic acids and/or water-soluble salts of acrylic acids. The water-soluble salts of acrylic acids are alkaline metal salts, alkaline earth metal salts, ammonium salts, hydroxy ammonium salts, amine salts and alkyl amine salts of acrylic acids having a neutralization rate within a range of from 30 mole percent to 100 mole percent, more preferably within a range of from 50 mole percent to 99 mole percent. Among the exemplified water-soluble salts, sodium salt and potassium salt are more preferred. These acrylate monomers may be used individually or in combination. When the unsaturated monomer contains an acrylate monomer as a chief constituent, the amount of monomers other than the acrylate monomer is preferably less than 40 weight percent, more preferably less than 30 weight percent, and most preferably less than 10 weight percent of the total unsaturated monomer. By using the monomers other than the acrylate monomer in the above mentioned ratio, the water absorption characteristics of the resulting water-absorbent resin are further improved, and the water-absorbent resin can be obtained at further reduced costs.

In certain embodiments, the present invention relates to a crosslinked gel, comprising a hydrophobic polymer; and a compound represented by 1 or 2 and any of their respective attendant definitions.

In certain embodiments, the present invention relates to a crosslinked gel as defined above, wherein said hydrophobic polymer comprises an alkyl acrylate, alkyl alkylacrylate, alkyl acrylamide, or alkyl alkylacrylamide.

In certain embodiments, the present invention relates to a crosslinked gel as defined above, wherein said hydrophobic polymer comprises an alkyl methacrylate.

In certain embodiments, the present invention relates to a crosslinked gel as defined above, wherein said hydrophobic polymer comprises methyl methacrylate, ethyl methacrylate, n-butyl methacrylate, or tert-butyl methacrylate.

In certain embodiments, the present invention relates to a crosslinked hydrogel, comprising a hydrophilic polymer; and a compound represented by 1 or 2 and any of their respective attendant definitions.

In certain embodiments, the present invention relates to a crosslinked hydrogel as defined above, wherein said hydrophilic polymer comprises an acrylic acid, acrylate, or acrylamide.

In certain embodiments, the present invention relates to a crosslinked hydrogel as defined above, wherein said hydrophilic polymer comprises acrylic acid, 2-hydroxyethyl acrylate, oligo(ethylene glycol) 2-methacrylate, acrylamide, N,N-dimethylacrylamide, or N-(tris(hydroxymethyl)methyl)acrylamide.

In certain embodiments, the present invention relates to a crosslinked hydrogel as defined above, wherein said hydrophilic polymer consists of a first acrylamide and a second acrylamide.

In certain embodiments, the present invention relates to a crosslinked hydrogel as defined above, wherein said first acrylamide is acrylamide or N,N-dimethylacrylamide.

In certain embodiments, the present invention relates to a crosslinked hydrogel as defined above, wherein said second acrylamide is N-(tris(hydroxymethyl)methyl)acrylamide.

In certain embodiments, the present invention relates to a crosslinked hydrogel as defined above, wherein said first acrylamide is acrylamide or N,N-dimethylacrylamide; and said second acrylamide is N-(tris(hydroxymethyl)methyl)acrylamide.

In certain embodiments, the present invention relates to a crosslinked hydrogel as defined above, wherein said hydrophilic polymer consists of an acrylamide and an acrylate.

In certain embodiments, the present invention relates to a crosslinked hydrogel as defined above, wherein said acrylamide is acrylamide or N,N-dimethylacrylamide.

In certain embodiments, the present invention relates to a crosslinked hydrogel as defined above, wherein said acrylate is acrylic acid, 2-hydroxyethyl acrylate, or oligo(ethylene glycol) 2-methacrylate.

In certain embodiments, the present invention relates to a crosslinked hydrogel as defined above, wherein said acrylamide is acrylamide or N,N-dimethylacrylamide; and said acrylate is acrylic acid, 2-hydroxyethyl acrylate, or oligo(ethylene glycol) 2-methacrylate.

In certain embodiments, the present invention relates to a crosslinked hydrogel as defined above, wherein said hydrophilic polymer consists of a first acrylate and a second acrylate.

In certain embodiments, the present invention relates to a crosslinked hydrogel as defined above, wherein said first acrylate is acrylic acid, 2-hydroxyethyl acrylate, or oligo(ethylene glycol) 2-methacrylate.

In certain embodiments, the present invention relates to a crosslinked hydrogel as defined above, wherein said first acrylate is acrylic acid, 2-hydroxyethyl acrylate, or oligo (ethylene glycol) 2-methacrylate; and said second acrylate is acrylic acid, 2-hydroxyethyl acrylate, or oligo(ethylene glycol) 2-methacrylate.

Methods of the Invention

The polymerization methods of the present invention may be practiced in water, organic solvents, or a mixture of both. The concentration of the unsaturated monomer in the solution (hereinafter referred to as the monomer solution) is exemplified in a non-limiting manner within this description as preferably but not exclusively including a range of from 20 weight percent to 65 weight percent, more preferably from 25 weight percent to 60 weight percent, most preferably from 30 weight percent to 45 weight percent.

As noted above, it is also possible to use water and an organic solvent soluble in water together as a solvent for the monomer solution. Examples of suitable organic solvents are methyl alcohol, ethyl alcohol, acetone, dimethyl sulfoxide, ethylene glycol monomethyl ether, glycerin, (poly) ethylene glycol, (poly)propylene glycol, and alkylene carbonate. These organic solvents may be used individually, or in combination.

Finally, also as noted above, a pure organic solvent may be used for the monomer solution.

The polymerization method is not particularly limited, and various methods can be used. Examples include radical polymerization using a radical polymerization initiator, irradiation-induced polymerization, electron radiation-induced polymerization, and ultraviolet-induced polymerization using a photosensitizer. Among these methods, radical polymerization is preferred.

As for the radical polymerization step, there are various polymerization methods, such as aqueous solution polymerization, cast polymerization which is performed within a mold, thin-layer polymerization which is performed on a belt conveyer, polymerization which is performed while making generated hydrogel polymer into small pieces, reversed-phase suspension polymerization, reversed-phase emulsion polymerization, precipitation polymerization, and bulk polymerization. Among these polymerization methods, the aqueous solution polymerization which polymerizes the unsaturated monomer in the form of aqueous solution is more preferred because the polymerization temperature can be easily controlled. The aqueous solution polymerization of the unsaturated monomer may be performed either continuously or batch-wise, or may be performed under suction, pressure, or atmospheric pressure. Generally, it is preferred to dissolve or disperse a radical polymerization initiator in an monomer solution in advance. Examples of the radical polymerization initiator include: peroxides, such as ammonium persulfate, potassium persulfate, sodium persulfate, hydrogen peroxide, benzoyl peroxide, cumene hydroperoxide, and di-t-butyl peroxide; redox initiators formed by combining the above-mentioned peroxides and reducing agents, such as sulfite, bisulfite, thiosulfate, formamidine sulfinic acid, and ascorbic acid; acrylic acid salts of azo-compound containing an amino group represented by general formula (1) or (2) above; and azo polymerization initiators, such as hydrochlorides of the azo-compound containing an amino group. These radical polymerization initiators may be used individually, or in combination. The amount of the radical polymerization initiator with respect to the unsaturated monomer is varied depending on the combination of the unsaturated monomer and the radical polymerization initiator. However, the amount of the radical polymerization initiator to be used is within a range of preferably from 0.0005 weight parts to 5 weight parts, more preferably from 0.005 weight parts to 2.5 weight parts, based on 100 parts by weight of the unsaturated monomer. If the amount of the radical polymerization initiator is less than 0.0005 weight parts, the amount of unreacted unsaturated monomers increases, causing an unfavorable increase of the residual monomer content in the resulting water-absorbent resin. Although the temperature at the initiation of polymerization varies depending on the type of a radical polymerization initiator used, it is preferably within a range of from 30° C. to 120° C., more preferably from 40° C. to 80° C.

In certain embodiments, the present invention relates to a method of preparing a polymer comprising a monomer represented by 1 and the attendant definitions, comprising reacting a monomer represented by 1 and the attendant definitions with a second monomer in the presence of an initiator.

In certain embodiments, the present invention relates to a method of preparing a polymer comprising a monomer represented by 2 and the attendant definitions, comprising reacting a monomer represented by 2 and the attendant definitions with a second monomer in the presence of an initiator.

In certain embodiments, the present invention relates to a method of preparing a crosslinked gel comprising a monomer represented by 1 or 2 and the attendant definitions, comprising reacting a monomer represented by 1 or 2 and the attendant definitions with a hydrophobic monomer in the presence of an initiator.

In certain embodiments, the present invention relates to a method of preparing a crosslinked gel comprising a monomer represented by 1 or 2 and the attendant definitions, comprising reacting a monomer represented by 1 or 2 and the attendant definitions with a hydrophilic monomer in the presence of an initiator.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of Glutaroyl Dihydroxamic Acid (C5NHOH)

As shown in FIG. 1, the dihydroxamic acids were prepared through the reaction between the corresponding diester and hydroxylamine. For instance, the reaction of dimethyl glutarate (DBE-5, dibasic ester) with hydroxylamine produced C5NHOH. In a 1000 mL breaker containing 400 mL of methanol, DBE-5 (100 g, 0.6 mol) was added with stirring. This was followed by the addition of an aqueous solution of hydroxylamine (88.8 g, 50 wt % in water; 1.34 mol). This reaction was allowed to proceed for 85 h at room temperature. Then, the resulting C5NHOH was precipitated by introducing 400 mL of ethanol into the above reaction mixture, filtrated under vacuum and washed three times with ethanol. The product thus obtained was vacuum-dried at 40° C. for more than 48 h and a white powder was obtained with a yield of 66% based on the feed amount of DBE-5. $^1$H NMR measurement indicated that the peak at 3.68 ppm due to the methyl ester groups of DBE-5 disappeared completely after reaction and two new peaks corresponding to —NH— (10.37 ppm) and —OH (8.68 ppm) emerged quantitatively. Therefore, the ester groups were changed to hydroxamic acid groups completely.

Example 2

Preparation of Malonyl Dihydroxamic Acid (C3NHOH)

Malonyl dihydroxylamic acid was prepared according to the procedure outlined in Example 1, but with dimethyl malonate instead of dimethyl glutarate.

Example 3

Preparation of Succinyl Dihydroxamic Acid (C4NHOH)

Succinyl dihydroxylamic acid was prepared according to the procedure outlined in Example 1, but with dimethyl succinate instead of dimethyl glutarate.

Example 4

Preparation of Adipoyl Dihydroxamic Acid (C6NHOH)

C6NHOH was prepared by reacting dimethyl adipate (DBE-6, dibasic ester) with hydroxylamine in a mixture of methanol and water at room temperature. In a 1000 mL flask containing a magnetic stirring bar, methanol (500 mL) and DBE-6 (143 g, 0.813 mol) were sequentially added. The reaction started by introducing an aqueous solution of hydroxylamine (124 g of 50 wt % aqueous solution, 1.87 mol) into the above system. After the reaction proceeded for 48 h at room temperature, the mixture was concentrated by using a rotavapor and the product precipitated gradually. C6NHOH thus prepared was washed with cooled water (4° C.) three times. After vacuum-drying at 45° C. for 72 h, a white solid was obtained with a yield of 88% based on the feed amount of DBE-6 and its $^1$H NMR spectrum was consistent with the molecular structure of C6NHOH.

Example 5

Synthesis of N,N'-(dimethacryloyloxy)glutarylamide (C5NCL)

C5NCL was synthesized via the reaction between C5NHOH (prepared according to Example 1) and methacryloyl chloride. Well-dried glassware was used immediately after being taken out from the oven (120° C.). A four-neck 1000 mL round-bottom flask was equipped with a paddle stir, a dropping funnel with a pressure-equalization arm, a condenser and a thermometer. This reactor was degassed and replaced with nitrogen twice. Under nitrogen, well-dried C5NHOH (32.4 g, 0.20 mol) was first added, and this was followed by the addition of well-dried pyridine (50 mL) and DMF (260 mL). Then, methacryloyl chloride (41.4 mL, 0.4 mol) was diluted with DMF (40 mL) and added dropwise very slowly through the dropping funnel. After the reaction lasted 3 h at room temperature, 300 mL of chloroform was added and this mixture was poured into a large quantity of water (ca. 1000 mL) with vigorous starring. The organic phase was washed with water three times, dried with MgSO4 overnight and concentrated by evaporating chloroform off. Then, C5NHOH was obtained via crystallization from a mixture of ethyl ether and hexane. After vacuum-drying at 35° C. for 24 h, a white soft crystal was obtained with a yield of 34%. $^1$H NMR measurement indicated that after reaction, the resonance due to the hydroxyl group (8.68 ppm) of C5NHOH disappeared completely. The new peaks corresponding to the methacryloyl groups (CH$_2$=, 5.86 and 6.16 ppm; —CH$_3$, 1.94 ppm) emerged quantitatively, and the peak corresponding to —NH— group shifted from 10.37 to 11.71 ppm. The above results confirmed the formation of the new crosslinker C5NCL with designed molecular structure.

Example 6

Synthesis of N,N'-(dimethacryloyloxy)malonylamide (C3NCL)

Crosslinker N,N'-(dimethacryloyloxy)malonamide (C3NCL) was prepared according to the procedure outlined in Example 5, but with malonyl dihydroxamic acid (C3NHOH) prepared according to Example 2.

Example 7

Synthesis of N,N'-(dimethacryloyloxy)succinylamide (C4NCL)

Crosslinker N,N'-(dimethacryloyloxy)succinamide (C4NCL) was prepared according to the procedure outlined in Example 5, but with succinyl dihydroxamic acid (C4NHOH) prepared according to Example 3.

Example 8

Synthesis of N,N'-(dimethacryloyloxy)adipamide (C6NCL)

Using an apparatus similar to that for the preparation of C5NCL, C6NCL was prepared by reacting C6NHOH with methacryloyl chloride. C6NHOH (17.6 g, 0.1 mol) and a mixture of DMF (150 mL) and pyridine (40 mL) were charged first. Methacryloyl chloride (22 mL, 0.21 mol) was dissolved in 20 mL DMF and this solution was dropwise added within 35 min with stirring. After this reaction was allowed to last 2 h at 35° C., 200 mL of chloroform was added to dilute the reaction mixture. Then, 15 mL of concentrated hydrochloric acid was diluted with 200 mL of water and this solution was transferred into the above reaction system. In this manner, the mixture was separated to water and organic phases. The water phase was extracted with 50 mL of chloroform and this was combined with the organic phase. This chloroform solution was washed with water three times and dried with MgSO$_4$ overnight. When concentrated by evaporating, C6NCL precipitated as a white crystal, which was washed with ethyl ether twice and vacuum-dried overnight at 35° C. (yield: 38%). Its molecular structure and high purity (>99%) were confirmed by $^1$H NMR.

Example 9

Preparation of Hydrogels in Water

The crosslinkers of the present invention may be used for the synthesis of hydrogels in water or in an organic solvent or in mixture of aqueous and organic solvents. Here is an example for the preparation of 2-hydroxyethyl acrylate (HEA) hydrogel in water. C5NCL was first dissolved in DMF to obtain a 25 wt % solution. In a 100 mL round-bottom flask, HEA (2.0 g), C5NCL (0.4 g of 25 wt % DMF solution) and a mixed solvent (20 g) of glycerol and water (1:1 by volume) were added. This system was degassed, then re-filled with nitrogen twice. This flask was placed in an oil bath kept at 55° C. The polymerization was started by sequentially adding the initiator ammonium persulfate (APS, 50 mg) and the accelerator N,N,N,N-tetramethylethylenediamine (TMEDA, 0.1 mL). The hydrogel formed immediately and it was immersed in ethanol overnight, washed with ethanol and vacuum-dried for 20 h. As shown in Table 1, a series of hydrogels were prepared from different monomers, such as N,N-dimethylacrylamide (DMA), acrylic acid (AA), acrylamide (AAm), N-[tris(hydroxymethyl)methyl]acrylamide (TS), N-(hydroxymethyl)methacrylamide (HA), sodium acrylate (NaAA), and poly(ethylene glycol)-methacrylate (MW average 526).

TABLE 1

| Hydrogels prepared in water[a] | | |
| --- | --- | --- |
| Monomer | Crosslinker | Degradation Time[b] |
| TS | C5NCL | 22 days |
| HEA | C5NCL | 26 days |
| HMMA | C6NCL | 20 days |
| PEG-macromer | C6NCL | 31 days |
| AA | C5NCL | 8 h |
| NaAA | C6NCL | 6 h |
| DMA | C6NCL | 32 h |
| AAm | C6NCL | 7 h |

[a]Hydrogel formed with 5% crosslinker at 55° C.
[b]pH = 7.4, 37° C.

Example 10

Preparation of Copolymer Hydrogels

Under the conditions similar to those for homopolymer hydrogels, the copolymerization of two monomers in the presence of the new crosslinker generated corresponding copolymer hydrogels. Here is an example for the preparation of TS-AA copolymer hydrogel. In a 100 mL round-bottom flask containing a magnetic stirring bar, 1.8 g of TS was charged. This solid monomer was dissolved in a mixed solvent (20 g) of glycerol and distilled water (2:1 by volume). Then, AA (0.2 g) and C5NCL (0.4 g of 25 wt % DMF solution) were added at room temperature. This system was degassed under reduced pressure and replaced with nitrogen twice. When the temperature was raised to 60° C., APS (50 mg) and TMEDA (0.1 mL) were sequentially added to induce the polymerization. The copolymer hydrogel formed instantaneously, which was immersed in ethanol to remove the solvent, washed with ethanol and vacuum-dried over 20 h. Using a similar procedure, TS-AA and TS-DMA copolymer hydrogels with various compositions were prepared (see Table 2).

TABLE 2

| Copolymer hydrogels[a] | | |
| --- | --- | --- |
| Monomer 1 | Monomer 2 | Degradation Time[b] |
| HEA 90% | DMA 10% | 13 days |
| HEA 80% | DMA 20% | 9.5 days |
| HEA 90% | AA 10% | 4 days |
| PEA 80% | AA 20% | 2 days |
| TS 90% | DMA 10% | 7 days |
| TS 80% | DMA 20% | 4 days |
| TS 90% | AA 10% | 23 h |
| TS 80% | AA 20% | 15 h |

[a]Hydrogel formed with 5% C5NCL at 55° C.
[b]pH = 7.4 at 37° C.

Example 11

Preparation of (Hydro)Gels in Organic Solvents

Because the new crosslinkers are soluble in organic solvents, the hydrogels were also prepared in organic solvents. Here is an example of 2-hydroxyethl methacrylate (HEMA) hydrogel prepared in 1,4-dioxane. In a 100 mL round-bottom flask containing a magnetic stirring bar, HEMA (2.2 g) was dissolved in 1,4-dioxane (10 g). To this flask, C6NCL (2.2 g of 10wt % DMF solution) was added. This system was degassed under reduced pressure and replaced with nitrogen twice. When the temperature was raised to 60° C., 2,2'-anobisisobutyronitrile (AIBN, 35 mg in 1 mL of 1,4-dioxane) was added to induce the polymerization. The copolymer hydrogel formed in 65 min and the reaction was allowed to last additional 3 h. The hydrogel thus obtained was immersed in acetone to remove the solvent, washed with acetone and vacuum-dried overnight. Using a similar procedure, several kinds of hydrogels were prepared from different monomers, such as t-butyl acrylamide (BAA) and mono-2-(acryloyloxy)ethyl succinate (AES) (see Table 3).

TABLE 3

| Hydrogels prepared in organic solvent[a] | |
| --- | --- |
| Monomer | Crosslinker |
| HEMA 2.2 g | C6NCL 0.22 g |
| AES 2.0 g | C6NCL 0.18 g |
| BAA 2.3 g | C5NCL 0.15 g |

[a]Hydrogels prepared in 1,4-dioxane at 60° C.

Example 12

Preparation of TS Homopolymer Beads

A 500 mL open-mouth jacketed flask was equipped with a mixer, a thermometer and a temperature controller, to which 150 μL of mineral oil and 0.12 g of sorbitan sesquioleate (SSO) were sequentially added. This system was heated to 60° C. by circulating water with stirring (350 rpm), and used as the continuing oil phase.

Simultaneously, the water phase was prepared in a small beaker as follows. Sodium chloride (23.2 g) and sodium acetate (11.0 g) were first dissolved in distilled water (81.6 mL). Then, this aqueous solution was mixed with glycerol (163 mL) with magnetic stirring. Finally, the pH value of this mixture was regulated to 6.0 by adding acetic acid.

The buffer solution (pH=6, 26 mL) was used to dissolve TS (5.0 g). To this solution, the crosslinker C6NCL (0.3 g in 3.0 g DMF solution) was dropwise added with stirring. This mixture was heated to 60° C. in an oil bath. As soon as the initiator APS (0.2 g) was added, this water phase was transferred into the oil phase with fast stirring (650 rpm), and TMEDA (0.4 mL) was added immediately to accelerate the reaction. After the polymerization lasted 1 h, the mixture was rinsed into about 120 mL of water to separate the beads. The beads in water phase were washed with water for more than five times, then, immersed in a buffer (pH=2) and stored in the refrigerator (4° C.). [Bead size and distribution, minimum: 16.8; maximum: 793.1; D1,0 (Num. mean): 181.3; D2,0: 207.3; D4,3 (Vol. mean): 330.5]. In the buffer solution (pH=7.4) at 37° C., this type of bead degraded completely in 21 days.

Example 13

Preparation of TS-DMA Copolymer Beads

The oil phase preparation was carried out according to the procedure outlined in Example 12. However, instead of using one monomer, both TS and DMA were included in the water phase. TS constitutes the neutral polymer backbone, while DMA acts as the degradation controller. For instance, 4.5 g of TS was first dissolved in the buffer solution (26 g, pH=6. see Example 12) at 45° C. Then, 0.50 g of DMA and a DMF solution of the crosslinker C6NCL (10 wt %, 3 g) were dropwise added with stirring. This system was heated to 60° C. in an oil bath. Upon the addition of 0.20 g of APS, this mixture was poured into the oil phase and the accelerator TMEDA (0.40 mL dissolved in 2 mL mineral oil) was added immediately. About 1 h later, the beads thus obtained were purified in the way similar to that used in Example 8. [Bead size and distribution, minimum: 16.8; maximum: 893.3; D1,0 (Num. mean): 229.4; D2,0: 281.4; D4,3 (Vol. mean): 476.7]. In the buffer solution (pH=7.4) at 37° C., this type of bead degraded completely in 7 days.

Example 14

Preparation of Citroyl Trihydroxamic Acid (CTA)

Citroyl trihydroxamic acid (CTA) was synthesized through the exchange reaction between triethyl citrate and hydroxylamine. In a 1000 mL beaker with a paddle stirrer, methanol (400 mL) and triethyl citrate (112 g, 0.40 mol) were sequentially added. Then, the reaction was started by introducing an aqueous solution of hydroxylamine (50 wt %, 87 g, 1.3 mol) into the above mixture with stirring at room temperature. As the reaction was proceeding, the product, CTA, precipitated gradually. After 72 h, the solid CTA thus obtained was washed twice with methanol and vacuum-dried for 50 h at 45° C. Yield: 54% (based on the feed amount of triethyl citrate). $^1$H NMR spectra showed no peaks corresponding to an ethyl ester group; further, a very broad peak (5.35–11.00 ppm) was observed, corresponding to the N—H and O—H moieties of the hydroxamic acid groups.

Example 15

Preparation of Three-arm Star-shaped Crosslinker N,N,N-(trimethacryloyloxy)citrylamide (TMCA)

Using an apparatus similar to that for the preparation of C5NCL, the three-arm star-shaped crosslinker TMCA was synthesized. CTA was reacted with methacryloyl chloride (MCl). The molar ratio of MCl and CTA was roughly MCl/CTA=3.0. The general procedure was the same as that used in the synthesis of C5NCL. This star-shaped crosslinker was used for the preparation of both hydrogels and beads.

Example 16

Preparation of TS-DMA Copolymer Hydrogel by Using TMCA as Crosslinker

In a 100 mL round-bottom flask containing a magnetic stirring bar, 4.0 g of TS was added. This solid monomer was dissolved in a mixed solvent (40 g) of glycerol and distilled water (2:1 by volume). Then, DMA (1.0 g) and TMCA (1.0 g of 25 wt % DMF solution) were added at room temperature. This system was degassed under reduced pressure and replaced with nitrogen twice. The temperature was raised to 60° C., and APS (0.15 mg) and TMEDA (0.4 mL) were sequentially added to induce the polymerization. The copolymer hydrogel formed instantaneously, and was then immersed in ethanol to remove the solvent, washed with ethanol and vacuum-dried for 20 h. This hydrogel degraded in a buffer (pH=7.4) within 5 days at 37° C.

Example 17

Preparation of TS-DMA Copolymer Beads by Using TMCA as Crosslinker

The oil phase preparation was carried out according to the procedure described in Example 12. For the preparation of the water phase, 4.5 g of TS was first dissolved in a buffer solution (30 g, pH=6; see Example 12) at 45° C. Then, 0.50 g of DAM and a DMF solution of the crosslinker TMCA (25 wt %, 1.0 g) were added dropwise with stirring. This system was heated to 60° C. in an oil bath. Upon the addition of 0.15 g of APS, this mixture was poured into the oil phase and the accelerator TMEDA (0.40 mL dissolved in 2 mL mineral oil) was added. About 25 min later, the beads thus obtained were purified using the protocol described in Example 12. In a buffered solution (pH=7.4) at 37° C., the beads degraded completely in 4 days.

Example 18

Preparation of N-methacryloylhydroxylamine (MHA)

MHA was synthesized by reacting methyl methacrylate (MMA) with hydroxylamine in a basic aqueous solution. In a 700 mL beaker, hydroxylamine hydrochloride (70 g) was added, which was dissolved in 150 g of sterile water. The aqueous solution thus obtained was cooled to 0° C., to which MMA (100 g) was added. In another beaker, sodium hydroxide (80 g) was dissolved in sterile water (140 g). After cooling to 0° C., this basic aqueous solution was dropwise added to the first beaker with vigorous stirring. At this stage, the formation of MHA was confirmed by testing the reaction mixture with an acidic aqueous solution of ferric chloride; the deep-red color of the complex formed between MHA and $FeCl_3$ appeared instantaneously. After the reaction lasted 3 h at 0° C., the system was concentrated by distillation under reduced pressure and the residue was extracted with ether (6×200 mL). The ether phase was concentrated by evaporation and a solid product was obtained by crystallization from a mixture of ether and hexane. The $^1$H NMR spectrum of this crystal is consistent with the molecular structure of MHA (DMSO-$d_6$) —NHOH, 10.70 and 8.79 ppm; C=$CH_2$, 5.28 and 5.57 ppm; —$CH_3$, 1.82 ppm; and no impurities were detected.

Example 19

Preparation of Crosslinkers O,O'-di[(methacryloyl)amino]adipate (NCLC6)

NCLC6 was prepared through the reaction between MHA and adipoyl chloride. MHA (20.2 g, 0.2 mol) and a mixture of DMF (100 mL) and pyridine (20 mL) were charged first. Adipoyl chloride (18.7 g, 0.10 mol) was dissolved in 25 mL of DMF and this solution was dropwise added within 70 min with stirring. After this reaction was allowed to last 2 h at 23° C., 250 mL of chloroform was added to dilute the reaction mixture and this was followed by the addition of 200 mL of water. In this manner, the mixture was separated to provide aqueous and organic phases. The aqueous phase was extracted with 50 mL of chloroform and this extract was combined with the organic phase. This chloroform solution was washed with water three times and dried with $MgSO_4$ overnight. After the chloroform was removed by evaporation, the solid NCLC6 was obtained by crystallization from a mixture of ether and hexane. Its molecular structure and high purity (>99.5%) were confirmed by $^1$H NMR (DMSO-$d_6$): NH, 11.80 ppm; C=CH$_2$, 5.49 and 5.73 ppm; CH$_2$C=O, 2.52 ppm; —CH$_3$, 1.88 ppm; —CCH$_2$CH$_2$C—, 1.68 ppm.

Example 20

Preparation of TS-DMA Copolymer Beads by Using NCLC6 as Crosslinker

The oil phase preparation was carried out according to the procedure described in Example 12. For the preparation of the water phase, 4.5 g of TS was first dissolved in a buffer solution (30 g, pH=6. see Example 12) at 45° C. Then, 0.50 g of DMA and a DMF solution of the crosslinker NCLC6 (10 wt %, 4.5 g) were dropwise added with stirring. This system was heated to 60° C. in an oil bath. Upon the addition of 0.15 g of APS, this mixture was poured into the oil phase and the accelerator TMEDA (0.40 mL dissolved in 2 mL mineral oil) was added immediately. About 30 min later, the beads thus obtained were purified in the way similar to that used in Example 12. This kind of beads in the buffer solution (pH=7.4) degraded completely within 6 days at 37° C.

Example 21

Preparation of HEA-hydrogel Using NCLC6 as Crosslinker

NCLC6 was first dissolved in DMF to obtain a 10 wt % solution. In a 100 mL round-bottom flask, HEA (2.5 g), NCLC6 (2.5 g of 10 wt % DMF solution) and a mixed solvent (20 g) of glycerol and water (1:1 by volume) were added. This system was degassed, then, re-filled with nitrogen twice. This flask was placed in an oil bath kept at 55° C. The polymerization was started by sequentially adding the initiator ammonium persulfate (APS, 60 mg) and the accelerator N,N,N,N-tetramethylethylenediamine (TMEDA, 0.15 mL). The hydrogel formed immediately. The hydrogel thus prepared was vacuum-dried for two days at 30° C.

The degradation test was carried out in a buffer solution (pH=7.4) at 37° C. HEA-hydrogel degraded within 9 days. As shown in Table 4, a series of hydrogels were prepared from different monomers, such as N,N-dimethylacrylamide (DMA), acrylic acid (AA), acrylamide (AAm), N-[tris(hydroxymethyl)methyl]acrylamide (TS), by using NCLC6 as the crosslinker.

TABLE 4

Hydrogels prepared using NCLC6 as the crosslinker.

| Monomer (g) | NCLC6 (g) | Degradation Time (day) |
| --- | --- | --- |
| HEA 2.5 | 0.25 | 9 |
| TS 3.5 | 0.30 | 7 |
| AAm 5.0 | 0.40 | 2.5 |
| DMA 3.0 | 0.25 | 1.5 |
| AA 4.0 | 0.35 | 1 |

No degradation was seen after three weeks at pH 3 and 4° C.

Example 22

Preparation of HEA-DMA Copolymer Hydrogel Using NCLC6 as Crosslinker

Under the conditions similar to those for homopolymer hydrogels, the copolymerization of two monomers in the presence of the new crosslinker generated corresponding copolymer hydrogels. Here is an example for the preparation of HEA-DMA copolymer hydrogel. In a 100 mL round-bottom flask containing a magnetic stirring bar, HEA (1.3 g) and DMA (1.3 g) were charged. This mixture was dissolved in a mixed solvent (20 g) of glycerol and distilled water (2:1 by volume). Then, NCLC6 (2.5 g of 10 wt % DMF solution) was added at room temperature. This system was degassed under reduced pressure and replaced with nitrogen twice. When the temperature was raised to 60° C., APS (50 mg) and TMEDA (0.14 mL) were sequentially added to induce the polymerization. The copolymer hydrogel formed instantaneously, which was vacuum-dried for two days at 30° C.

The degradation test was carried out in a buffer solution (pH=7.4) at 37° C. HEA-DMA hydrogel degraded within 4 days. Using a similar procedure, HEA-AA, TS-AA and TS-DMA copolymer hydrogels with various compositions were prepared (see Table 5).

TABLE 5

Copolymer hydrogels prepared by using NCLC6 as the crosslinker.

| Monomer 1 (g) | Monomer 2 (g) | NCLC6 (g) | Degradation time (day) |
| --- | --- | --- | --- |
| HEA 1.3 | DMA 1.3 | 0.25 | 4 |
| HEA 2.5 | AA 1.5 | 0.30 | 3 |
| TS 1.3 | DMA 1.3 | 0.30 | 4 |
| TS 1.4 | AA 1.4 | 0.4 | 2 |

No degradation was seen after three weeks at pH 3 and 4° C.

Incorporation By Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A crosslinked hydrogel, comprising a hydrophilic polymer; and a crosslinker selected from the group consisting of a compound of formula 1 and a compound of formula 2, wherein said compound of formula 1 is represented by:

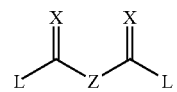

wherein

X represents independently for each occurrence O or S;

L represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1–10; and m represents independently for each occurrence an integer in the range 0–10; and said compound of formula 2 is represented by:

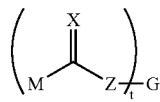

2 wherein

X represents independently for each occurrence O or S;

M represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

G represents (CR$_{(4-t)}$), aryl, or heteroaryl;

n represents independently for each occurrence an integer in the range 1–10; and t represents 3 or 4.

2. The crosslinked hydrogel of claim 1, wherein said hydrophilic polymer comprises an acrylic acid, acrylate, or acrylamide.

3. The crosslinked hydrogel of claim 1, wherein said hydrophilic polymer comprises acrylic acid, 2-hydroxyethyl acrylate, oligo(ethylene glycol) 2-methacrylate, acrylamide, N,N-dimethylacrylamide, or N-(tris(hydroxymethyl)methyl)acrylamide.

4. The crosslinked hydrogel of claim 1, wherein said hydrophilic polymer consists of a first acrylamide and a second acrylamide.

5. The crosslinked hydrogel of claim 4, wherein said first acrylamide is acrylamide or N,N-dimethylacrylamide.

6. The crosslinked hydrogel of claim 4, wherein said second acrylamide is N-(tris(hydroxymethyl)methyl)acrylamide.

7. The crosslinked hydrogel of claim 4, wherein said first acrylamide is acrylamide or N,N-dimethylacrylamide; and said second acrylamide is N-(tris(hydroxymethyl)methyl)acrylamide.

8. The crosslinked hydrogel of claim 4, wherein said hydrophilic polymer consists of an acrylamide and an acrylate.

9. The crosslinked hydrogel of claim 8, wherein said acrylamide is acrylamide or N,N-dimethylacrylamide.

10. The crosslinked hydrogel of claim 8, wherein said acrylate is acrylic acid, 2-hydroxyethyl acrylate, or oligo(ethylene glycol) 2-methacrylate.

11. The crosslinked hydrogel of claim 8, wherein said acrylamide is acrylamide or N,N-dimethylacrylamide; and said acrylate is acrylic acid, 2-hydroxyethyl acrylate, or oligo(ethylene glycol) 2-methacrylate.

12. The crosslinked hydrogel of claim 1, wherein said hydrophilic polymer consists of a first acrylate and a second acrylate.

13. The crosslinked hydrogel of claim 12, wherein said first acrylate is acrylic acid, 2-hydroxyethyl acrylate, or oligo(ethylene glycol) 2-methacrylate.

14. The crosslinked hydrogel of claim 12, wherein said first acrylate is acrylic acid, 2-hydroxyethyl acrylate, or oligo(ethylene glycol) 2-methacrylate; and said second acrylate is acrylic acid, 2-hydroxyethyl acrylate, or oligo(ethylene glycol) 2-methacrylate.

15. A method of preparing a crosslinked hydrogel, comprising a hydrophilic polymer and a crosslinker represented by 1:

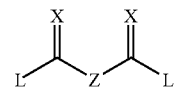

1 wherein

X represents independently for each occurrence O or S;

L represents independently for each occurrence —NH—O—Q, or —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO (CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents (CR$_2$)$_n$, (CR$_2$)$_n$J(CR$_2$)$_m$, or (CR$_2$)$_n$Ar(CR$_2$)$_m$;

Ar represents independently for each occurrence aryl or heteroaryl;

J represents independently for each occurrence O, S, NR, cycloalkyl, heterocyclyl, (CH$_2$CH$_2$O )$_n$, or (CH$_2$CH$_2$N(R))$_n$;

n represents independently for each occurrence an integer in the range 1–10; and m represents independently for each occurrence an integer in the range 0–10;

comprising:

a) reacting a monomer represented by 1 with a hydrophilic monomer in the presence of an initiator.

16. A method of preparing a crosslinked hydrogel, comprising a hydrophilic polymer and a crosslinker represented by 2:

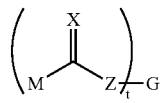

wherein
X represents independently for each occurrence O or S;
M represents independently for each occurrence —NH—O—Q, or —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;
R represents independently for each occurrence H or alkyl;
Z represents $(CR_2)_n$, $(CR_2)_nJ(CR_2)_m$, or $(CR_2)_nAr(CR_2)_m$;
Ar represents independently for each occurrence aryl or heteroaryl;
J represents independently for each occurrence O, S, NR, cycloalkyl, heterocyclyl, $(CH_2CH_2O)_n$, or $(CH_2CH_2N(R))_n$;
G represents $(CR_{(4-t)})$, aryl, or heteroaryl;
n represents independently for each occurrence an integer in the range 1–10; and
t represents 3 or 4;
comprising:
a) reacting a monomer represented by 1 with a hydrophilic monomer in the presence of an initiator.

17. The crosslinked hydrogel of claim 1, wherein said crosslinker is said compound of formula 1.

18. The crosslinked hydrogel of claim 17, wherein X represents O.

19. The crosslinked hydrogel of claim 17, wherein L represents —NH—O—Q.

20. The crosslinked hydrogel of claim 17, wherein L represents —O—NH—Q.

21. The crosslinked hydrogel of claim 17, wherein Q represents acryloyl, or 2-methacryloyl.

22. The crosslinked hydrogel of claim 17, wherein R represents H.

23. The crosslinked hydrogel of claim 17, wherein Z represents $(CR_2)_n$.

24. The crosslinked hydrogel of claim 17, wherein X represents O; and L represents —NH—O—Q.

25. The crosslinked hydrogel of claim 17, wherein X represents O; and L represents —O—NH—Q.

26. The crosslinked hydrogel of claim 17, wherein X represents O; L represents —NH—O—Q; and Q represents acryloyl, or 2-methacryloyl.

27. The crosslinked hydrogel of claim 17, wherein X represents O; L represents —O—NH—Q; and Q represents acryloyl, or 2-methacryloyl.

28. The crosslinked hydrogel of claim 17, wherein X represents O; L represents —NH—O—Q; Q represents acryloyl, or 2-methacryloyl; and R represents H.

29. The crosslinked hydrogel of claim 17, wherein X represents O; L represents —O—NH—Q; Q represents acryloyl, or 2-methacryloyl; and R represents H.

30. The crosslinked hydrogel of claim 17, wherein X represents O; L represents —NH—O—Q; Q represents acryloyl, or 2-methacryloyl; R represents H; and Z represents $(CR_2)_n$.

31. The crosslinked hydrogel of claim 17, wherein X represents O; L represents —O—NH—Q; Q represents acryloyl, or 2-methacryloyl; R represents H; and Z represents $(CR_2)_n$.

32. The crosslinked hydrogel of claim 1, wherein said crosslinker is said compound of formula 2.

33. The crosslinked hydrogel of claim 32, wherein X represents O.

34. The crosslinked hydrogel of claim 32, wherein M represents —NH—O—Q.

35. The crosslinked hydrogel of claim 32, wherein M represents —O—NH—Q.

36. The crosslinked hydrogel of claim 32, wherein Q represents acryloyl, or 2-methacryloyl.

37. The crosslinked hydrogel of claim 32, wherein R represents H.

38. The crosslinked hydrogel of claim 32, wherein X represents O; and M represents —NH—O—Q.

39. The crosslinked hydrogel of claim 32, wherein X represents O; and M represents —O—NH—Q.

40. The crosslinked hydrogel of claim 32, wherein X represents O; M represents —NH—O—Q; and Q represents acryloyl, or 2-methacryloyl.

41. The crosslinked hydrogel of claim 32, wherein X represents O; M represents —O—NH—Q; and Q represents acryloyl, or 2-methacryloyl.

42. The crosslinked hydrogel of claim 32, wherein X represents O; M represents —NH—O—Q; Q represents acryloyl, or 2-methacryloyl; and R represents H.

43. The crosslinked hydrogel of claim 32, wherein X represents O; M represents —O—NH—Q; Q represents acryloyl, or 2-methacryloyl; and R represents H.

* * * * *